US006865407B2

(12) United States Patent
Kimball et al.

(10) Patent No.: US 6,865,407 B2
(45) Date of Patent: Mar. 8, 2005

(54) CALIBRATION TECHNIQUE FOR NON-INVASIVE MEDICAL DEVICES

(75) Inventors: Victor E. Kimball, Burnsville, MN (US); Steven C. Furlong, Maple Grove, MN (US); Irvin Pierskalla, Prior Lake, MN (US)

(73) Assignee: Optical Sensors, Inc., Eden Prairie, MN (US)

( * ) Notice: Subject to any disclaimer, the term of this patent is extended or adjusted under 35 U.S.C. 154(b) by 221 days.

(21) Appl. No.: 10/195,120

(22) Filed: Jul. 11, 2002

(65) Prior Publication Data

US 2004/0010186 A1 Jan. 15, 2004

(51) Int. Cl.[7] .................................................. A61B 5/00
(52) U.S. Cl. ........................ 600/310; 600/317; 600/322
(58) Field of Search ................................ 600/309–310, 600/322, 311–312, 317

(56) References Cited

U.S. PATENT DOCUMENTS

| 5,355,880 | A |  | 10/1994 | Thomas et al. | |
|---|---|---|---|---|---|
| 5,533,509 | A |  | 7/1996 | Koashi et al. | |
| 5,697,366 | A |  | 12/1997 | Kimball et al. | |
| 5,792,050 | A |  | 8/1998 | Alam et al. | |
| 5,976,085 | A |  | 11/1999 | Kimball et al. | |
| 6,456,862 | B2 |  | 9/2002 | Benni | |
| 6,456,943 | B1 |  | 9/2002 | Kogure et al. | |
| 6,554,774 | B1 | * | 4/2003 | Miele ........................ | 600/485 |
| 6,587,704 | B1 | * | 7/2003 | Fine et al. ................... | 600/335 |
| 6,662,031 | B1 | * | 12/2003 | Khalil et al. ................. | 600/322 |
| 2004/0106874 | A1 | * | 6/2004 | Eigler et al. ................. | 600/486 |

FOREIGN PATENT DOCUMENTS

| WO | WO 92/20273 | 11/1992 |
|---|---|---|
| WO | WO 99/39631 | 8/1999 |
| WO | WO 02/24048 | 3/2002 |
| WO | WO 02/060320 | 8/2002 |

OTHER PUBLICATIONS

"Noninvasive Detection of a Physiologic Parameter Within a Body Tissue of a Patient", U.S. Appl. No. 10/162,028.
"Non–Invasive Measurement of pH"– attorney ref #1535.2US01.

* cited by examiner

Primary Examiner—Eric F. Winakur
Assistant Examiner—Matthew Kremer
(74) Attorney, Agent, or Firm—Barbara A. Wrigley; Oppenheimer Wolff & Donnelly LLP

(57) ABSTRACT

There is a need for a non-invasive method of calibrating medical devices at the point of care, where the calibration is performed without the removal of blood or bodily fluids. The invention is directed to an approach for calibrating a first non-invasive sensor in which the tissue being measured is modulated in some way so as to after the value of the parameter being measured by the first optical sensor. A second sensor detects another parameter that also changes with the modulation. The second sensor is absolutely calibrated. Where there is a known relationship between the first and second parameters, a calibration may be derived for the first sensor. Such a technique is applicable to calibrating non-invasive sensors for monitoring a wide variety of physiologic parameters including, inter alia, glucose, blood gases, blood electrolytes and blood pH.

54 Claims, 7 Drawing Sheets

CALIBRATION TECHNIQUE FOR NON-INVASIVE MEDICAL DEVICES

FIELD OF THE INVENTION

The present invention is directed generally to medical devices and more particularly to techniques to calibrate non-invasive devices.

BACKGROUND

Optical spectroscopy techniques have been developed for a wide variety of uses within the medical community. For example, pulse oximetry and capnography instruments are in widespread use at hospitals, both in the surgery suites and the post-op ICU's. These technologies have historically been based on absorption-based spectroscopy techniques and have typically been used as trend monitors in critical care environments where it is necessary to quickly determine if a patient's vital parameters are undergoing large physiologic changes. Given this operating environment, it has been acceptable for these devices to have somewhat relaxed precision and accuracy requirements, given the clinical need for real-time point-of-care data for patients in critical care situations.

Both pulse oximeters and capnography instruments can be labeled as non-invasive in that neither require penetrating the outer skin or tissue to make a measurement, nor do they require a blood or serum sample from the patient to custom calibrate the instrument to each individual patient. These instruments typically have pre-selected global calibration coefficients that have been determined from clinical trial results over a large patient population, and the results represent statistical averages over such variables as patient age, sex, race, and the like.

There is, however, a growing desire within the medical community for non-invasive instruments for use in such areas as the emergency room, critical care ICU's, and trauma centers where fast and accurate data are needed for patients in potentially life threatening situations. One such measurement needed in these environments is the blood and/or tissue pH level, which is a measure of the free hydrogen ion concentration. This is an important measure of intracellular metabolism. Biological processes within the human body require a narrow range of pH for normal function, and significant changes of pH from this range may be life threatening.

In addition to pH, it is also typical for the blood gases ($O_2$ and $CO_2$), blood electrolytes, and other blood chemistry parameters such as glucose, to be measured and monitored during critical care treatment. Technologies for making these measurements have been in place for nearly fifty years in hospital laboratories. These measurements are made from blood samples drawn from the patient which are then sent to a laboratory for analysis. These laboratory measurements are typically made with electrochemical sensors.

Recent developments in non-invasive optical technology hold the potential that some of these measurements may be made at the point of care with sufficient precision and accuracy to carry out critical care monitoring and treatment. For ease of use, and for meeting accuracy requirements, it is desirable that these non-invasive optical devices be custom calibrated to each individual patient at the point of care. The calibration technique should compensate for each individual's body chemistry and tissue make-up, including such things as collagen, elastin, and skin pigmentation, all of which affect skin and tissue optical properties. Ideally, the calibration technique for these optical sensors is quick, accurate, and easy to perform.

SUMMARY OF THE INVENTION

In view of the above discussion, there is a need to calibrate medical devices at the point of care, where the calibration is performed without the removal of blood or bodily fluids. Such a technique may be applicable to a wide variety of commonly monitored physiologic parameters during critical care patient management.

Generally, the present invention relates to an approach to calibrating a first non-invasive sensor in which the tissue being measured is modulated in some way so as to alter the value of the parameter being measured by the first sensor. A second sensor detects another parameter that also changes with the modulation. The second sensor is absolutely calibrated. Where there is a known relationship between the first and second parameters, a calibration may be derived for the first sensor.

One embodiment of the invention is directed to a method of calibrating a non-invasive sensor for determining a value of a first physiologic parameter within living tissue. The method includes non-invasively measuring first values of the first physiologic parameter and of a second physiologic parameter in the tissue. A known relationship exists between the first and second physiologic parameters. The tissue is acted on so as to change the first and second physiologic parameters. Second values of the first physiologic parameter and of the second physiologic parameter in the tissue are then measured. The measurements of the first and second values of the second physiologic parameter are absolutely calibrated. A calibrated value is then determined for at least one of the first and second values of the first physiologic parameter from the first and second values of both the first and second physiologic parameters.

Another embodiment of the invention is directed to a system for determining a value of a first physiologic parameter within tissue. The system includes first measuring means for non-invasively measuring first and second values of the first physiologic parameter in the tissue, and also includes second measuring means for non-invasively measuring first and second values of a second physiologic parameter in the tissue. A known relationship exists between the first and second physiologic parameters. The second measuring means is absolutely calibrated, the system also includes means for acting on the body so as to change the first and second physiologic parameters, and means for determining a calibrated value for at least one of the first and second values of the first physiologic parameter from the first and second values of both the first and second physiologic parameters.

Another embodiment of the invention is directed to an apparatus for determining a value of a first physiologic parameter within tissue. The apparatus includes an uncalibrated, first non-invasive sensor for measuring the first physiologic parameter of the tissue, and a calibrated, second non-invasive sensor for measuring a second physiologic parameter of the tissue. A processor is coupled to receive first and second signals from each of the first and second non-invasive sensors. The processor calculates a point-slope calibration for the first physiologic parameter from the first and second signals from each of the first and second non-invasive sensors when a characteristic of the tissue is modulated between the first and second signals.

The above summary of the present invention is not intended to describe each illustrated embodiment or every implementation of the present invention. The figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1A:
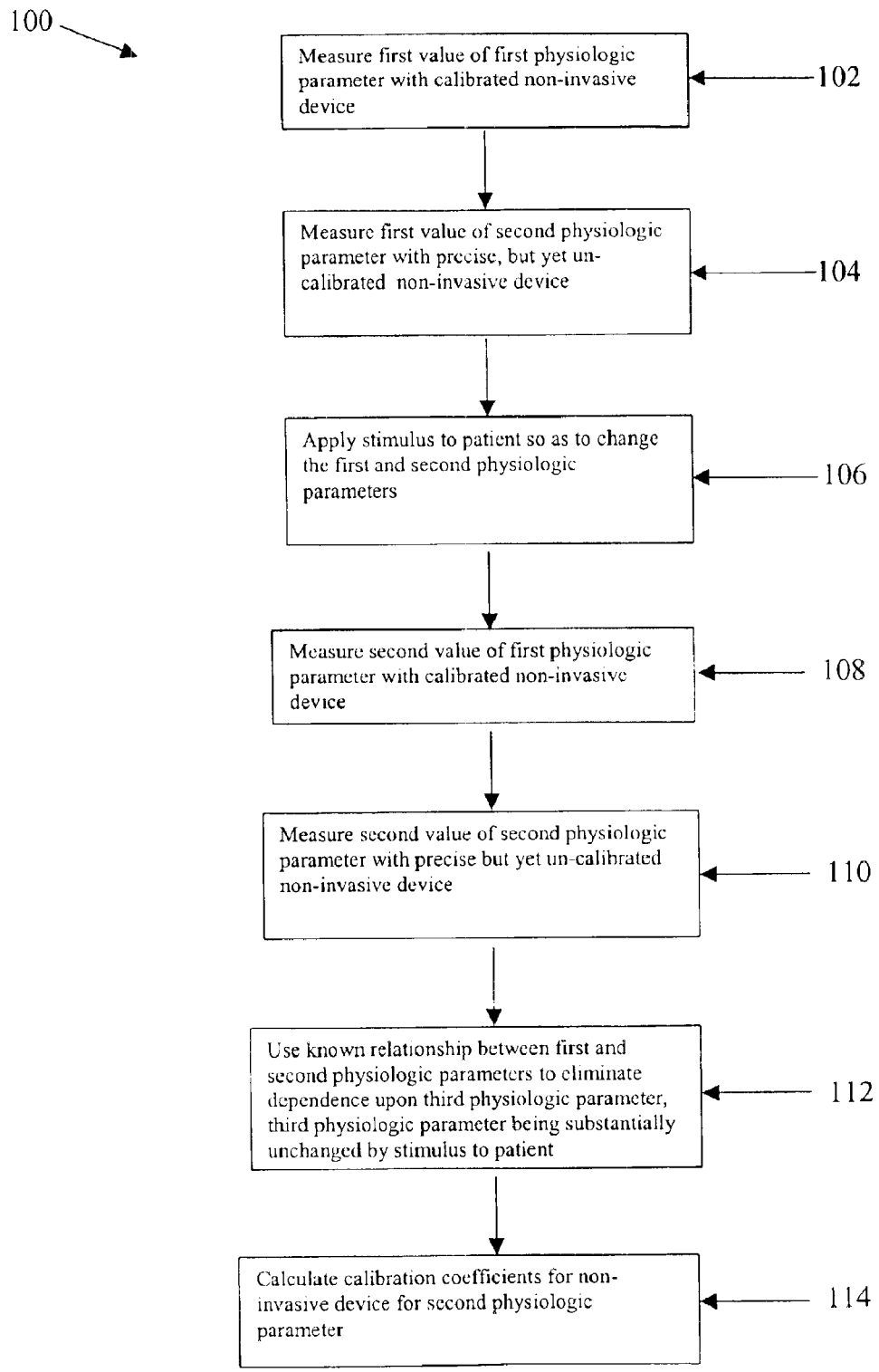
FIGS. 1A and 1B illustrate steps of different embodiments of a protocol to non-invasively calibrate a physiologic sensor, according to the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is applicable to medical devices and is believed to be particularly useful for calibrating non-invasive medical devices at the point of care.

According to one embodiment of the invention, a set of calibration coefficients is determined using the known chemical relationship between at least a first physiologic parameter (P1) and a second physiologic parameter (P2), where the physiologic parameters P1 and P2 can be measured non-invasively. For example, P1 and P2 may be related to optical spectra that be measured directly. Also, the technique can accommodate a third physiologic parameter (P3), which may participate in the equilibrium process between physiologic parameters P1 and P2. The measurable signal, S, can be characterized by equation (1), as follows:

$$S=S(P1, P2, P3) \tag{1}$$

That is, the measurable signal, S, is a function of the three physiologic parameters P1, P2, and P3. Given this dependence, it may require three independent data points to accurately calibrate such a system. It is however, commonplace in medical instrumentation to perform a two-point calibration prior to use which, for linear systems, is sometimes referred to as a point-slope calibration technique.

In one embodiment, the invention is directed to a technique to calibrate a medical device which has a measurable signal, S, whose dependence is governed by equation 1, in only two steps, by using a known relationship among the physiologic parameters P1, P2, and P3.

This technique may be expanded to include more complicated physiologic systems having a measurable signal, S' of the form:

$$S'=S'(P1, P2, P3 ---, Pn) \tag{2}$$

where, Pn is the $n^{th}$ physiologic parameter and use may be made of the relationship between the physiologic parameters to reduce the number of measurements needed. In the above case n measurements may be required if no relationship among the parameters is identified.

A list of steps of an embodiment of a protocol 100 to calibrate a non-invasive medical device is depicted in FIG. 1A. This particular embodiment is directed to a protocol for calibrating a device used to measure one physiologic parameter, P1, using calibrated measurements of a second parameter, P2. A known relationship, of the type listed as expression (1), exists between the first and second parameters via a third parameter, P3. In this particular case, the third parameter remains unchanged when a stimulus is applied to the patient.

The protocol 100 may yield quantitative results when a known chemical equilibrium/stoichiometry expression is known between the physiologic parameters of interest. In measurement step 102, the first physiologic parameter is measured with a non-invasive device that has been pre-calibrated for the first physiologic parameter. The first non-invasive device may measure the first physiologic parameter using any type of non-invasive modality, such as optical, electrochemical, acoustic, magnetic resonance, biochemical or osmotic assist.

Measurement step 104 determines the first value of the second physiologic parameter, the measurement 104 being taken with a non-invasive device which reports precise, but yet un-calibrated results. Like the first device, the device used for measuring the second physiologic parameter may use any suitable non-invasive modality, such as optical, electrochemical, acoustic, magnetic resonance, biochemical or osmotic assist. In one embodiment of the invention, the two measurement devices may be housed within the same mechanical structure. The measurements of the first and second physiologic parameters may take place at substantially the same time and at substantially the same physical location.

In protocol step 106, a stimulus is applied to the patient, the stimulus changing both the first and second physiologic parameters. In one embodiment of the invention, the stimulus in protocol step 106 is applied to the patient non-invasively. The stimulus may be applied at the same physical location that measurements 102 and 104 were taken.

Any suitable stimulus that affects the desired physiologic parameters may be used. It is important to understand that the stimulus applied to the patient may be a systemic change or a local change. A systemic change is one that is applied to a large part, or substantially all, of the patient's body, as might be expected, for example, with the application of one or more drugs.

A local stimulus is one that is applied to the patient's body in substantially only the location of the assay. For example, the application of localized pressure, localized induced temperature changes (heating and/or cooling), directed ultrasonic energy or the like, may result in local changes to physiologic parameters.

In protocol step 108, a second measurement of the first physiologic parameter is recorded with the calibrated non-invasive device. In protocol step 110, a second value of the second physiologic parameter is measured with the precise, but yet un-calibrated, non-invasive device.

The measurement steps 108 and 110 may be made at substantially the same time after application of the stimulus in step 106, or may be made while the stimulus is still being applied. In addition, the measurement steps 108 and 110 may be made at substantially at the same physical location as the measurements taken at steps 104 and 106.

At protocol step 112, the known relationship between the first and second physiologic parameters is used to eliminate the dependence upon any other physiologic parameter which may participate in the chemical equilibrium between the first and second physiologic parameters. The third physiologic parameter is substantially unchanged by the stimulus applied to the patient in step 106.

Where the known relationship between the first and second physiologic parameters involves one other physiologic parameter, a third physiologic parameter, then the third physiologic parameter may be eliminated using the first and second measurements of the first and second physiologic parameters. If the known relationship involves additional physiologic parameters, then additional measurements of the first and second physiologic parameters may be made at different levels of applied stimulus, and the additional measurements used to eliminate the additional physiologic parameters.

The calibration coefficients for the second physiologic parameter are calculated at protocol step 114. In the example case where the relationship between the first and second physiologic parameters includes only the third physiologic parameter, then the two calibrated data points may be used to calculate calibration coefficients for the non-invasive device for the second physiologic parameter.

The first and/or second parameters may be relatively time-independent, varying slowly with long-term physiological changes in the body over minutes or longer. The first and second parameters may also be time-variant. For example, blood gas and pH level may have pulsatile characteristics that depend on the pulsatile nature of the blood flow. On the other hand, physiologic parameters of the tissue bed, that are isolated from the pressure variations of pulsing arterial blood, are less likely to have pulsatile characteristics and are more likely to take on characteristics that drift over time.

Figure 1B:
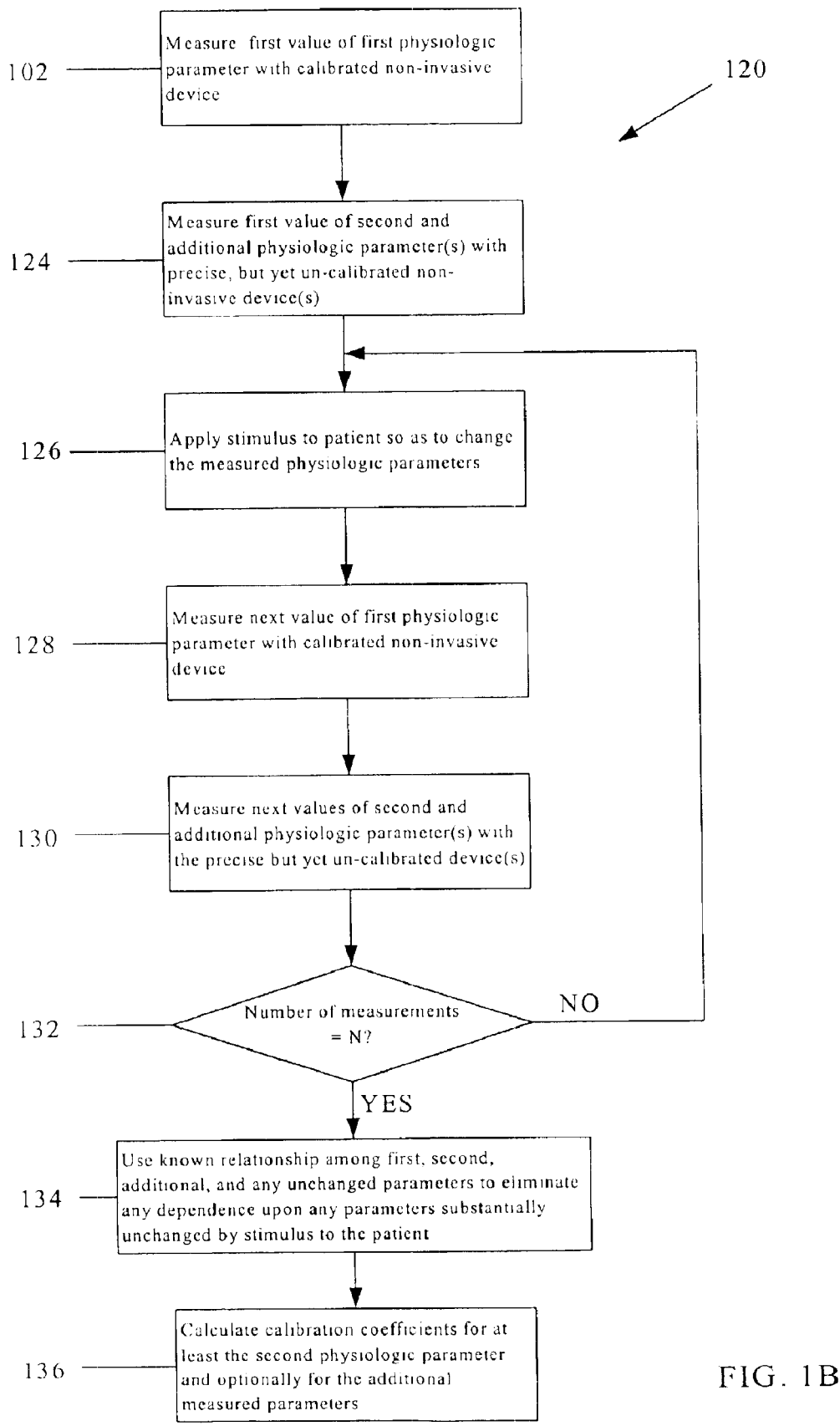

Another embodiment of a protocol 120 for calibrating a sensor for measuring a physiologic parameter P1 that is related to other parameters through a complex expression of the type described with reference to expression (2) is illustrated in FIG. 1B. The signal S' is related to n parameters, although not all n parameters necessarily change with application of the stimulus to the patient. Those parameters that do not change, or whose change is insignificant, under application of the stimulus to the patient may be treated in the analysis as constants. Accordingly, N sets of measurements need to be made, where N is the number of parameters that change with application of the stimulus.

The protocol 120 commences with a measurement of the first physiologic parameter using a calibrated sensor, at step 102. Next, first values of the second physiologic parameter, and additional physiologic parameters are measured, at step 124. The second physiologic parameter is the parameter whose sensor is being calibrated in the protocol, and is measured using a sensor that is un-calibrated but precise. The additional parameters may be measured using un-calibrated but precise sensors, or using calibrated sensors, or a combination of un-calibrated but precise, and calibrated sensors.

The stimulus is applied to the patient at step 126, so that the values of the measured physiologic parameters change.

At step 128, the next value of the first physiologic parameter is measured using the calibrated sensor. At step 130, the next values of the second parameter and the additional parameters are measured.

At step 132, a determination is made as to whether a sufficient number of measurements have been made. The number of measurements made for each parameter should be at least equal to the number parameters being measured, N. Each measurement for a parameter is made at a different level of applied stimulus, so that the parameter takes on a different value. If it is determined that an insufficient number of measurements has been taken, then the protocol returns to step 126 and the stimulus is applied at a new level so that the measured parameters adopt new values. The protocol continues to accumulate measurements of the different parameters at different levels of stimulus until the number of measurements reaches N.

Once it has been determined that a sufficient number of measurements has been made, the known relationship among the different measurements is used, at step 134, to eliminate any dependence on any parameters that do not significantly change under the stimulus. This permits calibration coefficients to be calculated for those physiologic parameters that were measured using precise, but yet un-calibrated sensors.

Figure 2:
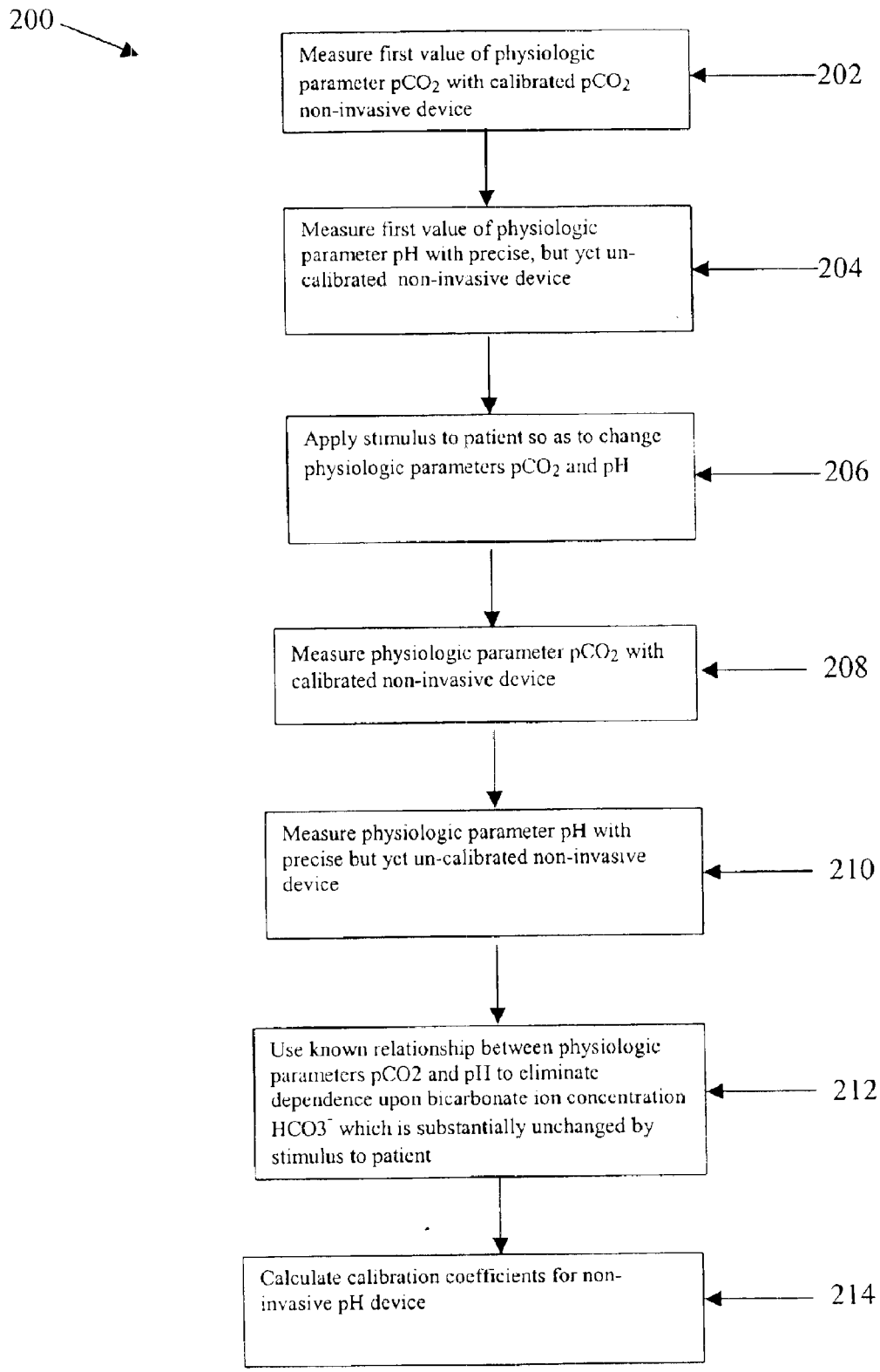
FIG. 2 illustrates steps of one embodiment of a protocol to non-invasively calibrate an optical pH physiologic sensor, according to the present invention.

FIG. 2 depicts steps of an embodiment of a protocol 200 to calibrate a non-invasive optical pH sensor. The protocol 200 may yield quantitative results when utilizing the relationship between the physiologic parameters given in equation (3), below:

$$pH = -\log([H^+]) = pK - \log([CO_2]/[HCO_3^-]) \quad (3)$$

where pH is the negative logarithm of the hydrogen ion concentration $[H^+]$, pK is the logarithm of the equilibrium constant, $[CO_2]$ is the carbon dioxide concentration, and $[HCO_3^-]$ is the bicarbonate ion concentration.

Under normal physiologic conditions the pH of human blood is maintained near 7.4 pH units. If, however, the pH drops below 6.8 (acidic) or rises above 7.8 (alkaline) the condition can become life threatening. Fortunately, the pH of human blood is buffered against such large deviations. For example, when moderate amounts of hydrogen ions, $H^+$, are added to blood during normal metabolic processes, the pH of blood is "buffered" against large swings. The reason is that the pH is dependent only on the ratio of $CO_2$ to bicarbonate ion (pK remains constant, unless the temperature changes), and under these conditions the $CO_2$ level is slightly elevated with an almost insignificant change in the bicarbonate level. The change in bicarbonate level is insignificant because the normal bicarbonate level is quite large, typically in the range of 23 to 25 milli-equivalents per liter. The protocol 200 utilizes this physiologic situation to simplify the calibration procedure of the non-invasive optical pH sensor as is outlined below. Accordingly, the change in bicarbonate level is taken to be substantially constant under localized changes of pH. Therefore, only two physiologic parameters, $CO_2$ and pH are measured, and so only two measurements for each parameter are required.

In measurement step 202, the first value of the $CO_2$ concentration is measured with a calibrated non-invasive device. In one embodiment of the invention, the $CO_2$ concentration may be measured indirectly by measuring the partial pressure of $CO_2$ of the tissue (commonly designated as $pCO_2$) generated in its gaseous form. The relationship between dissolved $CO_2$ and the $CO_2$ partial pressure, $pCO_2$, is given by equation 4, below:

$$\text{Total Carbon Dioxide dissolved} = \text{Solubility coefficient} * pCO_2 \quad (4)$$

Approaches for non-invasively measuring the $CO_2$ concentration of tissue include optical methods, such as near-infrared absorbance measurements. In particular, a method for measuring the $CO_2$ content of tissue using an optical approach is discussed in U.S. patent application Ser. No. 10/162,028 titled, "Non-invasive Detection of A Physiologic Parameter Within A Body Tissue of A Patient", by inventors Edward J. Anderson et al, which is incorporated herein by reference.

In step 204, the first value of physiologic parameter pH is measured, the measurement being taken with a non-invasive pH measuring device which reports precise but yet un-calibrated results. One approach to non-invasively measure pH is based around a measurement of the fluorescence of NADH, whose fluorescence efficiency is dependent on the local pH. This approach is discussed further in U.S. patent application Ser. No. 10/195,004 titled, "Non-invasive Measurement of pH", by inventors Victor Kimball, Steven Furlong, and Irvin Pierskalla, Altera Law Group Docket # 1535.2US01, filed on even date herewith, which is incorporated herein by reference.

In one embodiment of the invention, the $CO_2$ and pH measurement devices may be housed within the same mechanical structure and the measurements may take place at substantially the same time and at substantially the same physical location.

In protocol step 206, a stimulus is applied to the patient, the stimulus changing both the $CO_2$ and pH physiologic parameters. In one embodiment of the invention, the stimulus in protocol step 206 to the patient is applied non-invasively and the stimulus is applied at the same physical location that measurements 202 and 204 were taken.

Any suitable stimulus that affects the desired physiologic parameters may be used. The stimulus may affect the parameter directly or indirectly. Indirect affects may result, for example, by stopping blood flow to the tissue being assayed or by changing the metabolism of the tissue being assayed. An example of a direct effect is injecting a quantity of one of the physiologic parameters being measured, for example, glucose or electrolytes. A systemic change in the physiologic parameters may be expected, for example, after the administration of a drug that affects metabolism: the induced change in the body's metabolism results in a systemic change in the $CO_2$ and/or pH values of the patient, which may be measured at the measurement site.

A local stimulus, such as the application of localized pressure, localized induced temperature changes (heating and/or cooling), directed ultrasonic energy or the like, may also produce a change in the physiologic parameters. In addition, a drug may be administered so that it has a local effect, for example by being applied topically via a DMSO solution absorbed into the tissue.

Following application of the stimulus in step 206, a second measurement of the physiologic parameter $CO_2$ is recorded with the calibrated non-invasive device, at step 208. A measurement is also made, at step 210, to record a second value of the physiologic parameter pH with the precise but yet uncalibrated non-invasive device. In one embodiment of the invention, the measurement steps 208 and 210 may be made at substantially the same time after the stimulus in protocol step 206, and substantially at the same physical location as measurement steps 204 and 206. The measurements in steps 208 and 210 may be made while the stimulus is being applied or after the application of the stimulus has ceased.

At step 212, the known relationship between the physiologic parameters $CO_2$ and pH, as given by equation (3) is used to eliminate the dependence upon the bicarbonate ion concentration, [HCO3−], the bicarbonate ion concentration being substantially unchanged by the stimulus in protocol step 206 to the patient. This is described further below.

At protocol step 214, the two, or more, calibrated data points are used to calculate calibration coefficients for the non-invasive pH device.

One algebraic approach useful for calibrating the non-invasive pH device, according to the protocol 200, is outlined below. A short hand notation is employed to ease in following the calculations. Recall that the known relationship between pH and $CO_2$ concentration is given by the following expression:

$$pH = pK - \log([CO_2]/[HCO_3^-]) \quad (3)$$

or, utilizing $pH = -\log[H^+]$ and $pK = \log(K)$, equation (3) may be written as:

$$-\log[H^+] = \log(K) - \log([CO_2]/[HCO_3^-]) \quad (4)$$

Eliminating the logarithmic dependence, yields the expression:

$$-[H^+] = K - [CO_2]/[HCO_3^-] \quad (5)$$

Here we employ the following shorthand notation:
 $H_n$ = the $n^{th}$ measurement of the Hydrogen ion concentration, $[H^+]$
 $C_n$ = the $n^{th}$ measurement of the Carbon dioxide concentration, $[CO_2]$
 $B_n$ = the $n^{th}$ measurement of the Bicarbonate ion concentration, $[HCO_3^-]$ We can write the result of correlating the results of measurement steps 202 and 204 as:

$$-H_1 = K - (C_1/B_1) \quad (6)$$

Similarly, after applying the stimulus to the patient in protocol step 206, the result of correlating the measurements in steps 208 and 210 yields $$-H_2 = K - (C_2/B_1) \quad (7)$$

Where we have utilized the fact that the pK remains constant, i.e., $K_1 = K_2$, and the bicarbonate level remains substantially unchanged by the stimulus, $B_1 = B_2$. Given this, we can solve for the bicarbonate concentration by subtracting equation 6 from equation 7, which yields $$B_1 = (C_2 - C_1)/(H_2 - H_1) \quad (8)$$

Equation (8) highlights an important aspect of the present invention. The precise, but yet uncalibrated non-invasive pH measuring device utilized in measurement steps 204 and 210, yields accurate differential pH data ($H_2 - H_1$), thereby giving an accurate value for the bicarbonate level as given by equation (8). The accurate result for the bicarbonate level can be substituted back into equations (6) and (7)

$$-H_1 = K - (C_1/B_1) \quad (6)$$

$$-H_2 = K - (C_2/B_1) \quad (7)$$

Therefore, all terms on the right-hand side of equations (6) and (7) are now accurately known and a two-point calibration of the pH measurement device can be calculated directly from these results.

It will be appreciated that the protocols described above with reference to FIGS. 1A, 1B and 2 may be used also for quality assurance following calibration. To illustrate, consider the specific example discussed above with reference to FIG. 2 concerning a pH sensor. Once the pH sensor has been calibrated, it may be used over a prolonged period, for example for many minutes, or some hours, taking measurements of pH at regular intervals. It is useful to perform periodic quality assurance checks to ensure that the sensor has not drifted out of calibration. This may be done, after taking a measurement of pH and $CO_2$, by applying the stimulus to the patient and re-measuring the levels of pH and $CO_2$ under the stimulus. The calibration coefficients for the pH sensor may be recalculated and compared to those currently in use. If the newly calculated calibration coefficients are within an acceptable error range of the current coefficients, then use of the current coefficients may continue, or the coefficients may be automatically updated with the new coefficients. If the newly calculated calibration coefficients are outside the acceptable error range, then the coefficients are typically updated with the new values. The user may also be notified that the coefficients have been changed.

Figures 3A, 3B, 3C:
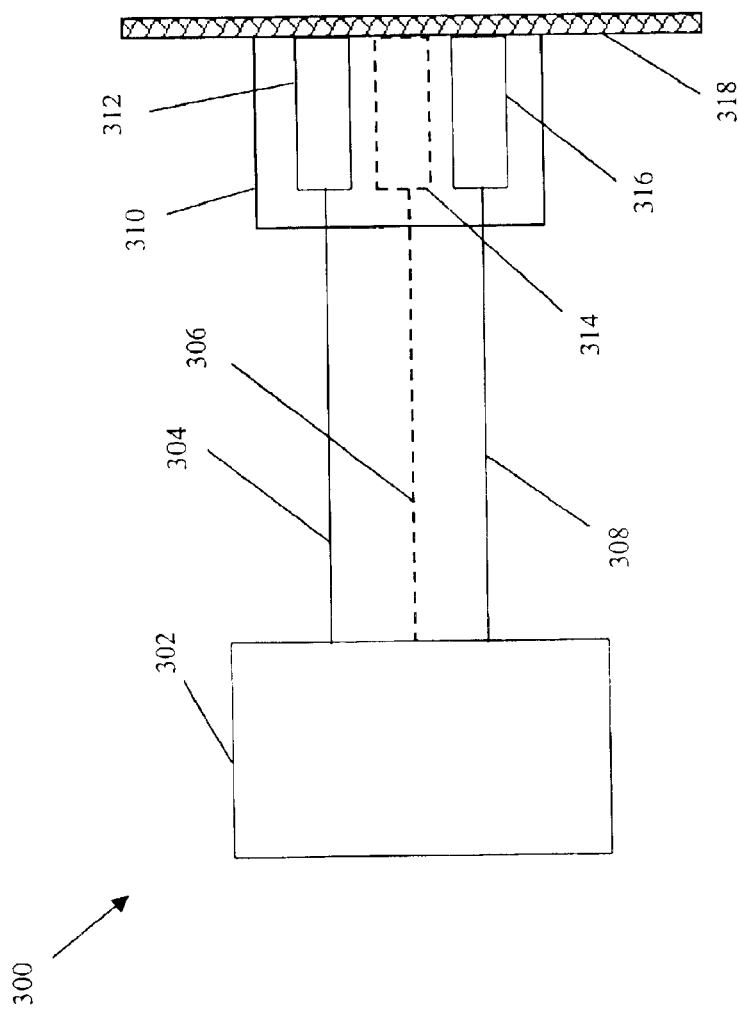
FIGS. 3A–3D schematically illustrate embodiments of a physiologic sensor module to non-invasively calibrate a physiologic sensor, according to the present invention.

One particular embodiment of a non-invasive physiologic monitoring device 300 is schematically depicted in FIG. 3A. A processor/controller module 302 may contain various sub-systems and a central processing unit to control the timing, delivery, routing and post processing of signals for the monitoring device 300. An interface 304 connects the controller module 302 to a first non-invasive physiologic sensor 312, which may be housed in a patient interface module 310. The first non-invasive sensor may be based on any type of non-invasive sensor including, but not restricted to, optical, electro-chemical, acoustic, magnetic resonance, biochemical or osmotic assist. In the case of an optical sensor, the interface 304 is an optical interface, and may include a fiber optic waveguide or a fiber optic bundle, or discrete bulk optical components such as a condensing lens or a series of condensing lenses. The patient interface module 310 may provide protection from such unwanted outside influences as stray light, fluid spills, and the like. The first non-invasive physiologic sensor 312 may be in direct physical contact with the patient's tissue surface 318. The tissue may be organ tissue, epithelial tissue, skin or any other type of tissue that is being assayed non-invasively.

An interconnect device 306 connects the controller module 302 with an optional stimulus transducer 314, which may also be housed in the patient interface module 310. The stimulus transducer 314 is advantageously included in the patient interface module 310 when the stimulus applied to the patient is a local stimulus, although it may also be included when the applied stimulus is systemic.

An interface 308 connects the controller module 302 with a second non-invasive physiologic sensor 316, which may also be housed in the patient interface module 310. In this configuration, the stimulus transducer 314 and the non-invasive sensors 312 and 316 may be mounted sufficiently close so that the same location of the tissue 318 is both stimulated and measured. Where the second non-invasive sensor 316 is an optical sensor, the interface 308 is typically an optical interface.

An example of an end-on view of the interface module 310 is schematically represented in FIG. 3B, showing the non-invasive physiologic sensors 312$b$ and 316$b$ and the stimulus transducer 314$b$. Another example of an end-on view of the interface module 310 is schematically represented in FIG. 3C, showing the relative locations of the non-invasive physiologic sensors 312$c$ and 316$c$ relative to the stimulus transducer 314$c$. It will be appreciated that other configurations may be used in addition to those illustrated in FIGS. 3A–3C. The spacing between the first physiologic sensor and the stimulus transducer may be the same as the distance between the second physiologic sensor and the stimulus transducer. In such a case, the tissue assayed by the first sensor is advantageously subject to the same magnitude of stimulus as the tissue assayed by second sensor.

Figure 3D:
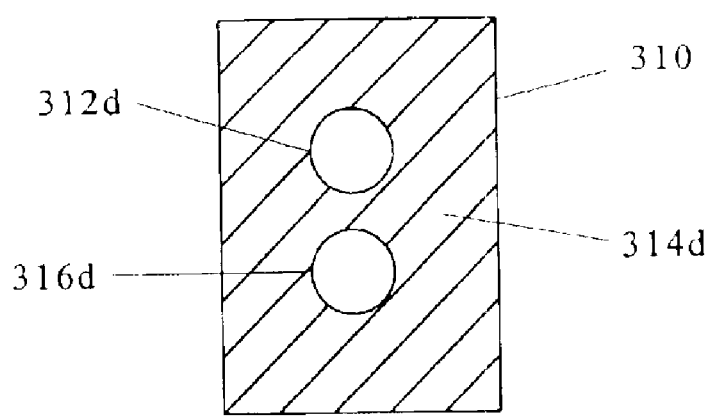

Another embodiment of an interface module 310 is schematically illustrated in FIG. 3D, in which a large portion 314$d$ of the face represents the stimulus transducer. The physiologic sensors 312$d$ and 316$d$ are surrounded by the stimulus transducer 314$d$. Such an embodiment advantageously ensures that the level of stimulus applied to the site assayed for the first physiologic parameter is similar to that applied to the site assayed for the second physiologic parameter.

Figure 4:
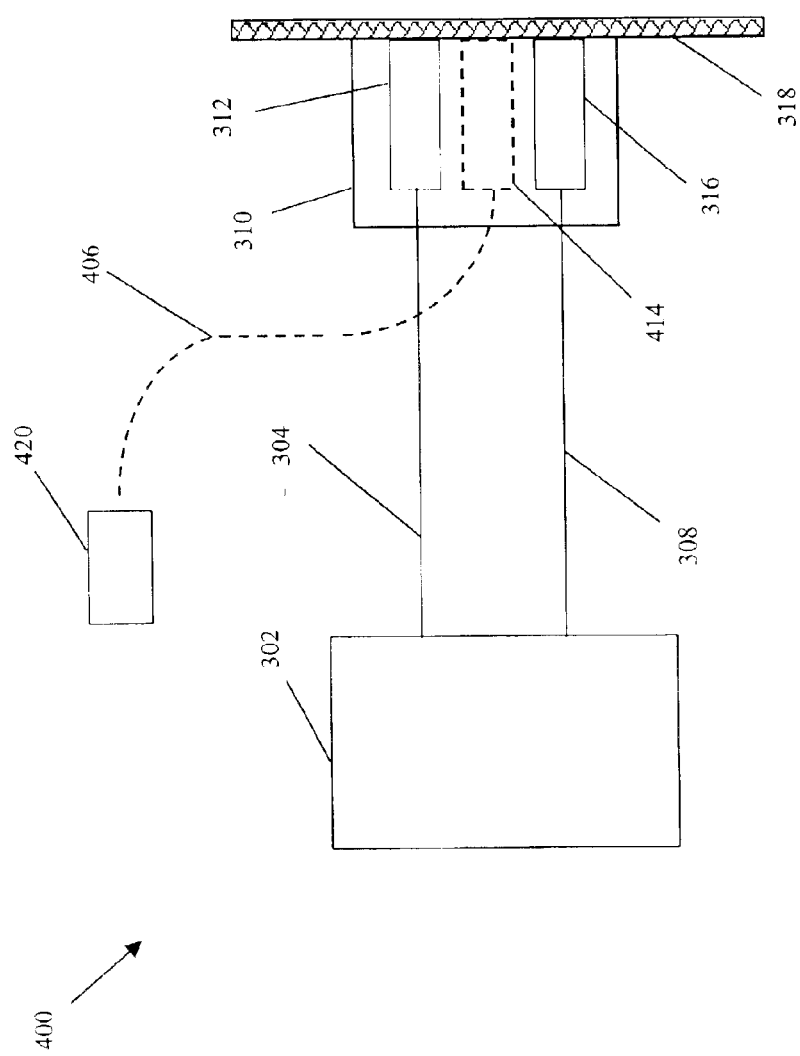
FIG. 4 schematically illustrates another embodiment of a physiologic sensor module to non-invasively calibrate a sensor, according to the present invention.

FIG. 4 schematically depicts another embodiment of the invention. Elements that are the same as shown in FIG. 3A are labeled with the same reference number. In this embodiment, the stimulus transducer 414 is not integrated within the patient interface module 310, and external controller unit 420 is a stand-alone unit separate from the main controller/processor unit 302. In this embodiment, the stimulus transducer 414 may be removed from the patient when the device is not being calibrated, or may be left in place. The stimulus transducer may also be used for occasional quality assurance checks while the device is in use. The stimulus transducer 414 may also be replaced by alternative devices which stimulate the patient's tissue 318 by pressure, temperature, acoustic or other such appropriate stimulating techniques.

Figure 5:
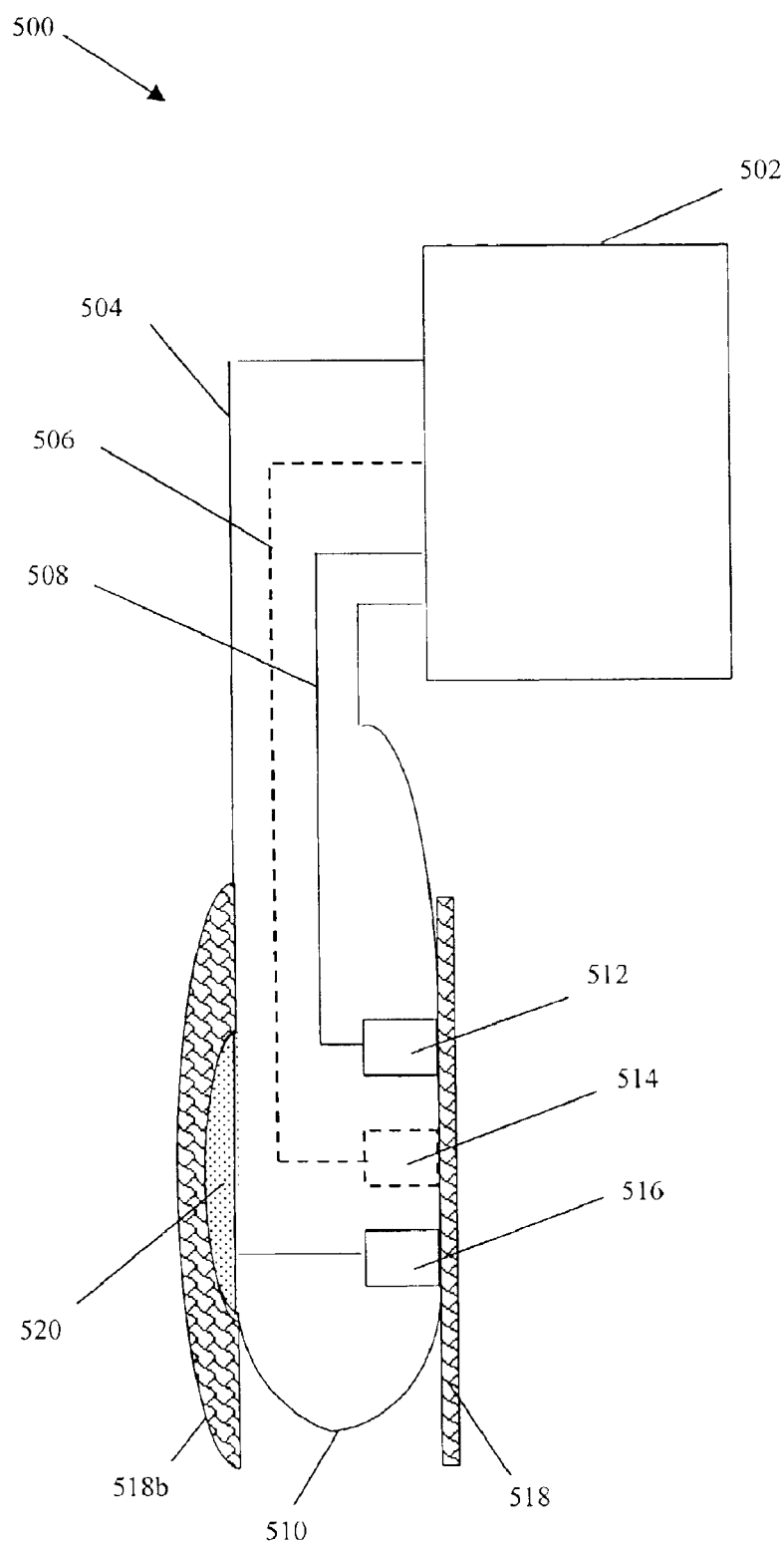
FIG. 5 schematically illustrates an embodiment of a physiologic sensor module to non-invasively calibrate an optical physiologic sensor placed in-situ in a body cavity or orifice, according to the present invention.

A particular embodiment of an optically based, non-invasive physiologic monitoring device 500 is depicted in FIG. 5. This embodiment may be particularly useful for conducting assays in a lumen, such as the esophagus. A processor/controller module 502 may contain the electro-optic sub-systems and a central processing unit to control the timing, delivery, routing and post processing of signals for the monitoring device 500. An optical interface 504 connects the controller module 502 to a first non-invasive optical physiologic sensor 512, which may be housed in a patient interface module 510. The optical interface 504 may be a fiber optic waveguide or a fiber optic bundle, or discrete bulk optical components such as a condensing lens or a series of condensing lenses. The patient interface module 510 may provide protection from such unwanted outside influences as stray light, fluid spills, and the like. The first non-invasive optical physiologic sensor 512 may be in direct physical contact with the patient's tissue surface 518. The interconnect device 506 connects the controller module 502 with the stimulus transducer 514, which may also be housed in the patient interface module 510. The optical interface 508 connects the controller module 502 with a second non-invasive optical physiologic sensor 516, which may also be housed in the patient interface module 510. In this configuration, the stimulus transducer 514 and the non-invasive optical sensors 512 and 516 may be mounted sufficiently close so as to stimulate and measure the tissue response at substantially the same physical location.

An inflatable bladder 520 may be incorporated into the patient interface module 510 for those applications where the sensor is inserted into a body cavity or orifice. This embodiment is advantageous in applications where it is desirable to apply pressure from the back surface 518$b$ of the patient's epithelial tissue surface 518$b$ to either mechanically secure the sensor against slippage during measurement or to apply additional pressure stimulus to aid in the calibration process. Other patient interface geometries and alternative sensor configurations are described in U.S. patent application Ser. No. 10/162,028 titled, "Non-invasive Detection of A Physiologic Parameter Within A Body Tissue of A Patient", by inventors Edward J. Anderson et al, which is incorporated herein by reference.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

For example, a patient monitor that includes sensors for measuring pH and $CO_2$ may be combined with other sensors for measuring other physiologic parameters, such as $O_2$ sat, $O_2$, hematocrit, and the like.

We claim:

1. A method of calibrating a non-invasive sensor for a first physiologic parameter in tissue, comprising:
   (a) non-invasively measuring first values of the first physiologic parameter and of a second physiologic parameter in the tissue, a known relationship existing between the first and second physiologic parameters;
   (b) acting on the tissue so as to change the first and second physiologic parameters;
   (c) non-invasively measuring second values of the first physiologic parameter and of the second physiologic parameter in the tissue, the measurements of the first and second values of the second physiologic parameter being absolutely calibrated; and
   (d) determining a calibrated value for at least one of the first and second values of the first physiologic parameter from the first and second values of both the first and second physiologic parameters;
   wherein non-invasively measuring the first values of the first physiologic parameter includes exciting the tissue with excitation light and detecting a resulting fluorescent signal.

2. A method as recited in claim 1, wherein non-invasively measuring the first and second values of the first parameter include measuring light received from the tissue.

3. A method as recited in claim 1, wherein non-invasively measuring the first and second values of the second parameter include measuring light received from the tissue.

4. A method as recited in claim 1, wherein the values for the first and second physiologic parameters are measured in the same region of the tissue.

5. A method as recited in claim 1, wherein acting on the tissue includes applying a systemic stimulus to the tissue.

6. A method as recited in claim 5, wherein applying a systemic stimulus to the tissue includes changing a metabolic rate of the tissue.

7. A method as recited in claim 1, wherein acting on the tissue includes applying a stimulus to the tissue localized to a region of the tissue where the first and second physiologic parameters are non-invasively measured.

8. A method as recited in claim 1, wherein acting on the tissue includes applying pressure to a region of the tissue where the first and second physiologic parameters are measured.

9. A method as recited in claim 1, wherein acting on the body includes changing temperature of a region of the body where the first and second physiologic parameters are measured.

10. The method of claim 1 wherein non-invasively measuring the first values of the first physiologic parameter further includes measuring tight absorbed by the tissue.

11. The method of claim 1 wherein non-invasively measuring the first values of the first physiologic parameter further includes measuring light reflected by the tissue.

12. A method of calibrating a non-invasive sensor for a first physiologic parameter in tissue of a patient, comprising:
   (a) non-invasively measuring first values of the first physiologic parameter and of a second physiologic parameter in the tissue, a known relationship existing between the first and second physiologic parameters;
   (b) administering a drug to the patient to change the first and second physiologic parameters;
   (c) non-invasively measuring second values of the first physiologic parameter and of the second physiologic parameter in the tissue, the measurements of the first and second values of the second physiologic parameter being absolutely calibrated; and
   (d) determining a calibrated value for at least one of the first and second values of the first physiologic parameter from the first and second values of both the first and second physiologic parameters.

13. A method as recited in claim 12, wherein non-invasively measuring the second values of the first physiologic parameter and of the second physiologic parameter includes measuring the second values of the first physiologic parameter and of the second physiologic parameter simultaneously.

14. A method of calibrating a non-invasive sensor for a first physiologic parameter in tissue, comprising:
   (a) non-invasively measuring first values of the first physiologic parameter and of a second physiologic parameter in the tissue, a known relationship existing between the first and second physiologic parameters, wherein the first physiologic parameter is pH;
   (b) acting on the tissue so as to change the first and second physiologic parameters;
   (c) non-invasively measuring second values of the first physiologic parameter and of the second physiologic parameter in the tissue, the measurements of the first and second values of the second physiologic parameter being absolutely calibrated; and
   (d) determining a calibrated value for at least one of the first and second values of the first physiologic parameter from the first and second values of both the first and second physiologic parameters.

15. A method as recited in claim 14, wherein measuring the pH includes making a fluorescence measurement of NADH in the region of the tissue being measured.

16. A method as recited in claim 14, wherein the second physiologic parameter is concentration of CO2.

17. A method as recited in claim 14, wherein the known relationship between the first and second physiologic parameters is $$pH=pK-\log([CO2]/[HCO3-])$$

where [CO2] is the second physiologic parameter.

18. A method as recited in claim 14, wherein the known relationship relates N physiologic parameters that change upon acting on the tissue so as to change the first and second physiologic parameters, and acting on the tissue N-1 times so as to take N measurements of each of the N physiologic parameters at different levels of stimulus arising from the acting on the tissue.

19. A method as recited in claim 14, further comprising non-invasively measuring the second values of the first physiologic parameter and of the second physiologic parameter in the tissue while acting on the tissue.

20. A method of calibrating a non-invasive sensor for a first physiologic parameter in tissue, comprising:
(a) non-invasively measuring first values of the first physiologic parameter and of a second physiologic parameter in the tissue, a known relationship existing between the first and second physiologic parameters that includes a third physiologic parameter substantially unaffected by the acting on the body;
(b) acting on the tissue so as to change the first and second physiologic parameters;
(c) non-invasively measuring second values of the first physiologic parameter and of the second physiologic parameter in the tissue, the measurements of the first and second values of the second physiologic parameter being absolutely calibrated; and
(d) determining a calibrated value for at least one of the first and second values of the first physiologic parameter from the first and second values of both the first and second physiologic parameters.

21. A method as recited in claim 20, wherein determining the calibrated value for at least one of the first and second values of the first physiologic parameter includes determining a value of the third physiologic parameter from a ratio of i) the difference between the first and second values of the second physiologic parameter over ii) the difference between the first and second values of the first physiologic parameter.

22. A method as recited in claim 21, wherein determining the calibrated value for at least one of the first and second values of the first physiologic parameter further includes calculating the calibrated value using the value of the third physiologic parameter and at least the respective calibrated first or second value of the second physiologic parameter.

23. A method of calibrating a non-invasive sensor for a first physiologic parameter in tissue, comprising:
(a) non-invasively measuring first values of the first physiologic parameter and of a second physiologic parameter in the tissue, a known relationship existing between the first and second physiologic parameters;
(b) acting on the tissue so as to change the first and second physiologic parameters;
(c) non-invasively measuring second values of the first physiologic parameter and of the second physiologic parameter in the tissue, the measurements of the first and second values of the second physiologic parameter being absolutely calibrated; and
(d) determining a calibrated value for at least one of the first and second values of the first physiologic parameter from the first and second values of both the first and second physiologic parameters;
wherein the tissue is epithelial tissue.

24. A method as recited in claim 23, wherein the tissue is selected from skin tissue and organ tissue.

25. A method as recited in claim 23, further comprising performing successive non-invasive measurements of the first physiologic parameter of the tissue and determining respective absolute calibrated values of the first physiologic parameter from the first and second values of both the first and second physiologic parameters.

26. A method as recited in claim 25, further comprising repeating steps (a)–(c) after performing the successive non-invasive measurements and determining whether a calibration of an instrument for non-invasively measuring the first physiologic parameter has changed.

27. An apparatus for determining a value of a first physiologic parameter within tissue, comprising:
an uncalibrated, first non-invasive pH sensor for measuring the first physiologic parameter of the tissue;
a calibrated, second non-invasive sensor for measuring a second physiologic parameter of the tissue; and
a processor coupled to receive first and second signals from each of the first and second non-invasive sensors, and to calculate calibrated values for the first physiologic parameter from the first and second signals from each of the first and second non-invasive sensors when a characteristic of the tissue is modulated between the first and second signals.

28. An apparatus as recited in claim 27, wherein the first non-invasive sensor is an optically based sensor.

29. An apparatus as recited in claim 27, wherein the second non-invasive sensor is an optically based sensor.

30. An apparatus as recited in claim 27, wherein the second non-invasive sensor is a calibrated, non-invasive CO2 sensor.

31. An apparatus as recited in claim 27, wherein the pH sensor emits excitation light in the wavelength range 300 nm–400 nm.

32. An apparatus as recited in claim 27, wherein the pH sensor detects light emitted for the tissue in a wavelength range of 400–600 nm.

33. An apparatus as recited in claim 27, wherein the pH sensor detects fluorescence from NADH in the tissue.

34. An apparatus as recited in claim 27, further comprising a patient interface module to house the first and second non-invasive sensors.

35. An apparatus as recited in claim 27, further comprising a modulator to modulate the characteristic of the tissue at the region of the tissue where the first and second physiologic parameters are measured.

36. An apparatus as recited in claim 35, wherein the modulator includes an extensible member to apply pressure of the region of the tissue where the first and second physiologic parameters are measured.

37. An apparatus as recited in claim 35, wherein the modulator includes a thermally responsive member to change temperature of the region of the tissue where the first and second physiologic parameters are measured.

38. An apparatus as recited in claim 35, further comprising a patient interface module, the first and second non-invasive sensors and the modulator being housed within the patient interface module.

39. An apparatus as recited in claim 38, wherein the modulator is removable from the patient interface module, the fist and second non-invasive sensors being enabled to perform measurements on the first and second physiologic parameters respectfully after the modulator is removed from the patient interface.

40. An apparatus as recited in claim 27, wherein the processor calculates calibration constants for the first physiologic parameter from the first and second signals from each of the first and second non-invasive sensors.

41. An apparatus as recited in claim 40, wherein the processor produces calibrated values for the first physiologic parameter from measurement signals received from the first non-invasive sensor and the calibration constants.

42. An apparatus for determining a value of a first physiologic parameter within tissue, comprising:
an uncalibrated, first non-invasive sensor for measuring the first physiologic parameter of the tissue;

a calibrated, second non-invasive sensor for measuring a second physiologic parameter of the tissue; and a processor coupled to receive first and second signals from each of the first and second non-invasive sensors, and to calculate calibrated values for the first physiologic parameter from the first and second signals from each of the first and second non-invasive sensors when a characteristic of the tissue is modulated between the first and second signals;

wherein the processor calculates calibration constants for the first physiologic parameter from the first and second signals from each of the first and second non-invasive sensors;

wherein the processor produces calibrated values for the first physiologic parameter from measurement signals received from the first non-invasive sensor and the calibration constants; and, wherein the processor performs a check on the calibration constants by measuring the first and second physiologic parameters before and after application of a stimulus to the tissue.

43. A method of calibrating a non-invasive sensor for a first physiologic parameter in muscle tissue, comprising:

(a) non-invasively measuring first values of the first physiologic parameter and of a second physiologic parameter in the muscle tissue, a known relationship existing between the first and second physiologic parameters;

(b) acting on the muscle tissue so as to change the first and second physiologic parameters;

(c) non-invasively measuring second values of the first physiologic parameter and of the second physiologic parameter in the muscle tissue, the measurements of the first and second values of the second physiologic parameter being absolutely calibrated; and (d) determining a calibrated value for at least one of the first arid second values of the first physiologic parameter from the first and second values of both the first and second physiologic parameters.

44. An apparatus for determining a value of a first physiologic parameter within tissue, comprising:

(a) means for non-invasively measuring first values of the first physiologic parameter and of a second physiologic parameter in the tissue, a known relationship existing between the first and second physiologic parameters;

(b) means for acting on the tissue so as to change the first and second physiologic parameters;

(c) means for non-invasively measuring second values of the first physiologic parameter and of the second physiologic parameter in the tissue, the measurements of the first and second values of the second physiologic parameter being absolutely calibrated; and (d) moans for determining a calibrated value for at least one of the first and second values of the first physiologic parameter from the first and second values of both the first and second physiologic parameters;

wherein the means for non-invasively measuring the first values of the first physiologic parameter includes a means for exciting the tissue with excitation light and a means for detecting a resulting fluorescent signal.

45. The apparatus as recited in claim 44, wherein the means for non-invasively measuring the first and second values of the first parameter include means for measuring light received from the tissue.

46. The apparatus as recited in claim 44, wherein the means for non-invasively measuring the first and second values of the second parameter include means for measuring light received from the tissue.

47. The apparatus as recited in claim 44, wherein the values for the first and second physiologic parameters are measured in the same region of the tissue.

48. The apparatus as recited in claim 44, wherein the means for acting on the tissue includes means for applying a systemic stimulus to the tissue.

49. The apparatus as recited in claim 48, wherein the means for applying a systemic stimulus to the tissue includes means for changing a metabolic rate of the tissue.

50. The apparatus as recited in claim 44, wherein the means for acting on the tissue includes means for applying a stimulus to the tissue localized to a region of the tissue where the first and second physiologic parameters are non-invasively measured.

51. The apparatus as recited in claim 44, wherein the means for acting on the tissue includes means for applying pressure to a region of the tissue where the first and second physiologic parameters are measured.

52. The apparatus as recited in claim 44, wherein means for acting on the body includes means for changing temperature of a region of the body where the first and second physiologic parameters are measured.

53. The apparatus of claim 44 wherein the means for non-invasively measuring the first values of the first physiologic parameter further includes a means for measuring light absorbed by the tissue.

54. The apparatus of claim 44 wherein the means for non-invasively measuring the first values of the first physiologic parameter further includes a means for measuring light reflected by the tissue.

* * * * *

UNITED STATES PATENT AND TRADEMARK OFFICE
CERTIFICATE OF CORRECTION

PATENT NO. : 6,865,407 B2
DATED : March 8, 2005
INVENTOR(S) : Victor E. Kimball, Steven C. Furlong and Irvin Pierskalla It is certified that error appears in the above-identified patent and that said Letters Patent is hereby corrected as shown below:

<u>Title page,</u>
Item [57], ABSTRACT, delete "after", and insert -- alter --.

<u>Column 12,</u>
Line 3, delete "tight", insert -- light --.

<u>Column 14,</u>
Line 52, delete "fist", insert -- first --.

<u>Column 15,</u>
Line 37, delete "arid", insert -- and --.

<u>Column 16,</u>
Line 4, delete "moans", insert -- means --.

Signed and Sealed this

Twenty-fourth Day of May, 2005

JON W. DUDAS
*Director of the United States Patent and Trademark Office*